(12) United States Patent
Ter Riet et al.

(10) Patent No.: US 11,920,144 B2
(45) Date of Patent: Mar. 5, 2024

(54) RESISTANCE GENE AND LETTUCE PLANT RESISTANT TO DOWNY MILDEW

(71) Applicant: Enza Zaden Beheer B.V., Enkhuizen (NL)

(72) Inventors: Bas Ter Riet, Medemblik (NL); Geert Johannes De Boer, IJmuiden (NL); Ilja Roobeek, Dirkshorn (NL); Mathieu Andre Pel, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 171 days.

(21) Appl. No.: 17/268,540

(22) PCT Filed: Aug. 16, 2018

(86) PCT No.: PCT/EP2018/072249
§ 371 (c)(1),
(2) Date: Feb. 15, 2021

(87) PCT Pub. No.: WO2020/035145
PCT Pub. Date: Feb. 20, 2020

(65) Prior Publication Data
US 2021/0238626 A1 Aug. 5, 2021

(51) Int. Cl.
*C12N 15/82* (2006.01)
*A01H 6/14* (2018.01)
*C07K 14/415* (2006.01)

(52) U.S. Cl.
CPC ....... *C12N 15/8282* (2013.01); *A01H 6/1472* (2018.05); *C07K 14/415* (2013.01)

(58) Field of Classification Search
None
See application file for complete search history.

(56) References Cited

FOREIGN PATENT DOCUMENTS

WO    2014131857 A1    9/2014
WO    2017023486 A1    2/2017

OTHER PUBLICATIONS

Genbank Locus PLY75840.1 (Year: 2018).*
Marin et al. "Distribution of races and virulence factors of Bremia lactucae in the main lettuce production area in Brazil". Journal of Plant Pathology. 102:395-407. (Year: 2020).*
Wehner republishing Ryder et al. "Vegetable Cultivar Descriptions for North America—Lettuce (M-Z)". U.S. Agricultural Research Station, Salinas, California. Accessed via https://cucurbitbreeding.wordpress.ncsu.edu/2016/06/02/lettuce-m-z/ (Year: 2016).*
PNWHandbooks.org. "Lettuce (*Lactuca sativa*)—Downy Mildew". (Year: 2015).*
NCBI Reference Sequence: XP_023731234.1 (Year: 2021).*
Ebeda et al., Wild *Lactuca* Species, Their Genetic Diversity, Resistance to Disease and Pests, and Exploitation in Lettuce Breeding, European Journal of Plant Pathology, 2013, 138(3): 597-640.
McHale et al., The Genomic Architecture of Disease Resistance in Lettuce, Theoretical and Applied Genetics; International Journal of Plant Breeding Research 2008, 118(3): 565-580.
Morita-Yamauro et al., The *Arabidposis* Gene CAD1 Controls Programmed Cell Death in the Plant Immune System and Encodes a Protein Contianing a MACPF Domain, Plan and Cell Physiology 2005, 46(6): 902-912.
NCBI Database, MACPF Domain-Containing Protein At4g24290-like isoform X1 [*Lactuca sativa*] 2018.
Parra et al., Rationalization of Genes for Ressitance to Bremia lactucae in Lettuce, Euphytica 2016, 210(3): 309-326.
Huang et al. "Virus-induced gene silencing and its application in plant functional genomics," Sci China Life Sci, 2012, 55: 99-108.
International Search Report and Written Opinion for International Application No. PCT/EP2018/072249 dated Feb. 20, 2020.

* cited by examiner

*Primary Examiner* — Matthew R Keogh
*Assistant Examiner* — David R Byrnes
(74) *Attorney, Agent, or Firm* — Foley Hoag LLP; Brendan T. Jones; David E. Shore

(57) ABSTRACT

Provided herein is a lettuce plant that is resistant to downy mildew, more specifically a lettuce plant that has a mutated gene that confers broad spectrum resistance to oomycetes in lettuce. Also provided herein are a resistance gene and a method for obtaining a lettuce plant that is resistant to downy mildew, wherein the method includes the step of mutating a gene.

9 Claims, 9 Drawing Sheets

Specification includes a Sequence Listing.

Figure 3

|  | Bl:16 | Bl:17 | Bl:18 | Bl:19 | Bl:20 | Bl:21 | Bl:22 | Bl:23 | Bl:24 |
|---|---|---|---|---|---|---|---|---|---|
| Cobham Green | + | + | + | + | + | + | + | + | + |
| Green Towers | + | + | + | + | + | + | + | + | + |
| Vanity | + | + | + | + | + | + | + | + | + |
| SE01 | - | - | - | - | - | - | - | - | - |

|  | Bl:25 | Bl:26 | Bl:27 | Bl:28 | Bl:29 | Bl:30 | Bl:31 | Bl:32 | Bl:33 |
|---|---|---|---|---|---|---|---|---|---|
| Cobham Green | + | + | + | + | + | + | + | + | + |
| Green Towers | + | + | + | + | + | + | + | + | + |
| Vanity | + | + | + | + | + | + | + | + | + |
| SE01 | - | - | - | - | - | - | - | - | - |

Figure 4

| Position of amino acid 12 substitutions/ insertion#/ addition* in MACPF1R protein (SEQ ID No.4) | Amino acid substitution MACPF1-->MACPF1R |
|---|---|
| 25 | S->A |
| 84 | H->Y |
| 178 | I->M |
| 181 | Y->F |
| 204 | T->A |
| 235 | K->T |
| 236 | Y->F |
| #255-258 | XXXX->TKND |
| 329 | D->E |
| 450 | T->S |
| 586 | M->I |
| 588 | T->I |
| 589 | R->D |
| *590 | D |

Figure 5

|  | 10 | 20 | 30 | 40 | 50 | 60 |
|---|---|---|---|---|---|---|
| MACPF1  | MALKLPAAEA | ANVAIQSIGC | GYDISLDLRL | NYRMRRYHSD | IGSNPYRNCR | LIEIEEDEGR |
| MACPF1R | MALKLPAAEA | ANVAIQSIGC | GYDIALDLRL | NYRMRRYHSD | IGSNPYRNCR | LIEIEEDEGR |

|  | 70 | 80 | 90 | 100 | 110 | 120 |
|---|---|---|---|---|---|---|
| MACPF1  | DIVLPGGLLL | LNVPESIKCH | ESEHTRLHSD | VLSFPQMSEQ | FNQELSLSGK | IPSGLFNYVF |
| MACPF1R | DIVLPGGLLL | LNVPESIKCH | ESEYTRLHSD | VLSFPQMSEQ | FNQELSLSGK | IPSGLFNYVF |

|  | 130 | 140 | 150 | 160 | 170 | 180 |
|---|---|---|---|---|---|---|
| MACPF1  | DFSGNWKKDA | SSTKTLAFDG | VFISLYTVAL | EESHMVLCDH | VKKAVPSSWE | PALLARFIEK |
| MACPF1R | DFSGNWKKDA | SSTKTLAFDG | VFISLYTVAL | EESHMVLCDH | VKKAVPSSWE | PALLARFMEK |

|  | 190 | 200 | 210 | 220 | 230 | 240 |
|---|---|---|---|---|---|---|
| MACPF1  | VGTHVIVGVK | MGGKDVIYMK | QQHTSSLEPA | DVQKKLKEMA | DKRFLDSKQI | SQNDKYDITH |
| MACPF1R | VGTHVIVGVK | MGGKDVIYMK | QQHASSLEPA | DVQKKLKEMA | DKRFLDSKQI | SQNDIFDITH |

|  | 250 | 260 | 270 | 280 | 290 | 300 |
|---|---|---|---|---|---|---|
| MACPF1  | LRSADLDTSS | SYSY----KE | HLLSICRRRG | GSDDRNLKHN | EWLQTVQSEP | DVITMSFVPI |
| MACPF1R | LRSADLDTSS | SYSYIKNDKE | HLLSICRRRG | GSDDRNLKHN | EWLQTVQSEP | DVITMSFVPI |

|  | 310 | 320 | 330 | 340 | 350 | 360 |
|---|---|---|---|---|---|---|
| MACPF1  | SLLLKGVMGS | GFLSHAINLY | LRYKPPFEDL | PQFLDFQLPT | QWAPVFGLLS | RGPQHEQRSV |
| MACPF1R | SLLLKGVMGS | GFLSHAINLY | LRYKPPFEEL | PQFLDFQLPT | QWAPVFGLLS | RGPQHEQRSV |

|  | 370 | 380 | 390 | 400 | 410 | 420 |
|---|---|---|---|---|---|---|
| MACPF1  | TSLQFSFFGT | KLYVNTYPVD | VGKRPVTGLR | ISLNCERNNQ | LEIHLQHLSA | VPKFVQLEDS |
| MACPF1R | TSLQFSFFGT | KLYVNTYPVD | VGKRPVTGLR | ISLNCERNNQ | LEIHLQHLSA | VPKFVQLEDS |

|  | 430 | 440 | 450 | 460 | 470 | 480 |
|---|---|---|---|---|---|---|
| MACPF1  | VTEILNFDSH | DHKDYEKVQA | KNFDHVCTAT | VESEDEFAIV | TGAQLHVGDH | GSKKVLFLRL |
| MACPF1R | VTEILNFDSH | DHKDYEKVQA | KNFDHVCTAS | VESEDEFAIV | TGAQLHVGDH | GSKKVLFLRL |

|  | 490 | 500 | 510 | 520 | 530 | 540 |
|---|---|---|---|---|---|---|
| MACPF1  | HFSKLHGCIA | NRNPEWEVSP | VQKLDSSISF | MEVVYARQFQ | VPHAPLHEPK | FVGPTETMQK |
| MACPF1R | HFSKLHGCIA | NRNPEWEVSP | VQKLDSSISF | MEVVYARQFQ | VPHAPLHEPK | FVGPTETMQK |

|  | 550 | 560 | 570 | 580 | 590 | 600 |
|---|---|---|---|---|---|---|
| MACPF1  | LLKFVDTTEM | KRGPQDSPGY | WVVIGARLVV | DKGKISLRVK | YALPQILTR- | .......... |
| MACPF1R | LLKFVDTTEM | KRGPQDSPGY | WVVIGARLVV | DKGKISLRVK | YALPQILDD | .......... |

Figure 6 cDNA sequence *MACPF1* (SEQ ID No.1):

ATGGCGCTTAAGCTTCCAGCTGCTGAAGCTGCAAATGTTGCGATTCAGTCAATTGGAT
GTGGTTATGATATCTCGTTAGATCTGAGGCTTAATTATCGCATGCGTCGTTATCATTCA
GATATTGGTTCTAATCCATATAGAAATTGCCGTTTGATAGAAATTGAGGAAGATGAAG
GTAGAGATATTGTGCTTCCTGGTGGGCTTCTACTTCTCAATGTTCCCGAATCCATCAAA
TGTCATGAAAGCGAGCATACACGACTTCATTCTGATGTTCTTTCTTTTCCGCAGATGTC
GGAGCAATTCAATCAGGAATTATCATTATCCGGCAAAATTCCTTCAGGCCTCTTCAATT
ATGTGTTTGATTTTTCTGGAAATTGGAAGAAAGATGCATCAAGTACTAAAACCCTAGC
TTTTGATGGTGTTTTCATCTCTTTGTACACGGTTGCATTAGAAGAATCACACATGGTTC
TTTGTGATCACGTCAAGAAAGCTGTTCCATCTTCATGGGAGCCTGCTTTGTTAGCAAGG
TTTATCGAAAAATATGGCACTCATGTAATTGTGGGTGTAAAAATGGGTGGAAAAGATG
TGATATATATGAAACAACAGCATACATCATCCCTTGAGCCTGCTGATGTACAGAAAAA
GTTAAAGGAAATGGCAGACAAGAGATTTTTGGACTCTAAACAGATTTCACAAAATGA
CAAGTATGACATCACACATCTAAGATCTGCAGACTTAGACACCTCTAGCTCTTATTCTT
ACAAGGAGCATCTTTTAAGCATTTGCAGAAGGAGAGGTGGGAGTGATGACAGGAACC
TAAAACATAACGAGTGGTTACAAACCGTACAATCAGAACCAGATGTAATCACAATGT
CCTTTGTTCCAATAAGCTTGTTGCTAAAGGGTGTTATGGGAAGTGGATTCTTAAGTCAT
GCCATAAATCTTTATTTACGCTATAAACCTCCATTTGAAGACCTTCCTCAGTTTCTGGA
CTTCCAGCTACCGACACAGTGGGCCCTGTATTCGGTTTGTTGTCTCGTGGTCCACAAC
ATGAGCAGCGAAGTGTGACATCTTTACAGTTCAGCTTTTTGGGACCAAGCTCTACGT
GAACACCTATCCTGTCGATGTAGGTAAGAGGCCTGTAACAGGCCTCCGACTTTCCCTC
AATTGTGAAAGAAACAATCAGTTAGAGATCCATCTCCAGCACCTCTCCGCCGTCCCAA
AATTCGTCCAACTAGAAGACTCCGTAACCGAAATCCTCAATTTCGATTCCCACGATCA
TAAAGACTACGAAAAGGTCCAAGCGAAAAATTTCGACCATGTTTGCACAGCCACTGTC
GAGTCTGAAGACGAATTCGCAATCGTAACCGGGGCCCAGTTACATGTCGGGGATCAC
GGGTCTAAAAAAGTCCTCTTCCTACGCCTCCACTTCTCAAAACTACATGGTTGCATCGC
AAATAGGAATCCGGAATGGGAAGTGTCTCCGGTTCAGAAACTGGATTCTTCAATTTCT
TTCATGGAGGTGGTCTACGCACGACAATTTCAAGTCCCGCATGCCCCACTTCACGAAC
CGAAATTTGTGGGCCCGACGGAGACAATGCAGAAACTATTGAAGTTTGTGGACACAA
CGGAGATGAAGCGGGGCCCGCAAGATAGCCCAGGGTATTGGGTTGTCATAGGGGCTA
GACTTGTTGTGGATAAGGGAAAGATTTCTCTTCGAGTCAAGTACGCTTTGCCTCAGAT
GTTAACCCGATGA

Figure 7

Protein sequence *MACPF1* (SEQ ID No.2):

MALKLPAAEAANVAIQSIGCGYDISLDLRLNYRMRRYHSDIGSNPYRNCRLIEIEEDEGRDI
VLPGGLLLLNVPESIKCHESEHTRLHSDVLSFPQMSEQFNQELSLSGKIPSGLFNYVFDFSG
NWKKDASSTKTLAFDGVFISLYTVALEESHMVLCDHVKKAVPSSWEPALLARFIEKYGTH
VIVGVKMGGKDVIYMKQQHTSSLEPADVQKKLKEMADKRFLDSKQISQNDKYDITHLRS
ADLDTSSSYSYKEHLLSICRRGGSDDRNLKHNEWLQTVQSEPDVITMSFVPISLLLKGVM
GSGFLSHAINLYLRYKPPFEDLPQFLDFQLPTQWAPVFGLLSRGPQHEQRSVTSLQFSFFGT
KLYVNTYPVDVGKRPVTGLRLSLNCERNNQLEIHLQHLSAVPKFVQLEDSVTEILNFDSHD
HKDYEKVQAKNFDHVCTATVESEDEFAIVTGAQLHVGDHGSKKVLFLRLHFSKLHGCIA
NRNPEWEVSPVQKLDSSISFMEVVYARQFQVPHAPLHEPKFVGPTETMQKLLKFVDTTEM
KRGPQDSPGYWVVIGARLVVDKGKISLRVKYALPQMLTR

Figure 8 cDNA sequence *MACPF1R* (SEQ ID No.3):

ATGGCGCTTAAGCTTCCAGCTGCTGAAGCTGCAAATGTTGCGATTCAGTCAATTGGAT
GTGGTTATGATATCGCGTTAGATCTGAGGCTTAATTATCGCATGCGTCGTTATCATTCA
GATATTGGTTCTAATCCATATAGAAATTGCCGTTTGATAGAAATTGAGGAAGATGAAG
GTAGAGATATTGTGCTTCCTGGTGGGCTTCTACTTCTCAATGTTCCCGAATCCATCAAA
TGTCATGAAAGCGAGTATACACGACTTCATTCTGATGTTCTTTCTTTTCCGCAGATGTC
GGAGCAATTCAATCAGGAATTATCATTATCCGGCAAAATTCCTTCAGGCCTCTTCAATT
ATGTGTTTGATTTTTCTGGAAATTGGAAGAAAGATGCATCAAGTACTAAAACCCTAGC
TTTTGATGGTGTTTTCATCTCTTTGTACACGGTTGCATTAGAAGAATCACACATGGTTC
TTTGTGATCACGTCAAGAAAGCTGTTCCATCTTCATGGGAGCCTGCTTTGTTAGCAAGG
TTTATGGAAAAATTTGGCACTCATGTAATTGTGGGTGTAAAAATGGGTGGAAAAGATG
TGATATATATGAAACAACAGCATGCATCATCCCTTGAACCTGCTGATGTACAGAAAAA
GTTAAAGGAAATGGCAGACAAGAGATTTTTGGACTCTAAACAGATTTCACAAAATGA
CACGTTTGACATCACACATCTAAGATCTGCAGACTTAGACACCTCTAGCTCTTATTCTT
ACACAAAAAATGACAAGGAGCATCTTTTAAGCATTTGCAGAAGGAGAGGTGGGAGTG
ATGACAGGAACCTAAAACATAACGAGTGGTTACAAACCGTACAATCAGAACCAGATG
TAATCACAATGTCCTTTGTTCCAATAAGCTTGTTGCTAAAGGGTGTTATGGGAAGTGG
ATTCTTAAGTCATGCCATAAATCTTTATTTACGCTATAAACCTCCATTTGAAGAGCTTC
CTCAGTTTCTGGACTTCCAGCTACCGACACAGTGGGCCCCTGTATTCGGTTTGTTGTCT
CGTGGTCCACAACATGAGCAGCGAAGTGTGACATCTTTACAGTTCAGCTTTTTGGGA
CCAAGCTCTACGTGAACACCTATCCTGTCGATGTAGGTAAGAGGCCTGTAACAGGCCT
CCGACTTTCCCTCAATTGTGAAAGAAACAATCAGTTAGAGATCCATCTCCAGCACCTC
TCCGCCGTCCCAAAATTCGTCCAACTAGAAGACTCCGTAACCGAAATCCTCAATTTCG
ATTCCCACGATCATAAAGACTACGAAAGGTCCAAGCGAAAATTTCGACCATGTTTG
CACAGCCTCTGTCGAGTCTGAAGACGAATTCGCAATCGTAACCGGGGCCCAGTTACAT
GTCGGGGATCACGGGTCTAAAAAGTCCTCTTCCTACGCCTCCACTTCTCAAAACTAC
ATGGTTGCATCGCAAATAGGAATCCGGAATGGGAAGTGTCTCCGGTTCAGAAACTGG
ATTCTTCAATTTCTTTCATGGAGGTGGTCTACGCACGACAATTTCAAGTCCCGCATGCC
CCACTTCACGAACCGAAATTTGTGGGCCCGACGGAGACGATGCAGAAGCTATTGAAG
TTTGTGGACACAACGGAGATGAAGCGGGGCCCGCAAGATAGCCCAGGGTATTGGGTT
GTAATAGGGGCTAGACTTGTTGTGGATAAGGGAAAGATTTCTCTTCGAGTCAAGTACG
CTTTGCCTCAGATATTAATCGATGATTAGAA

Figure 9

Protein sequence *MACPF1R* (SEQ ID No.4):

MALKLPAAEAANVAIQSIGCGYDIALDLRLNYRMRRYHSDIGSNPYRNCRLIEIEEDEGRDI
VLPGGLLLLNVPESIKCHESEYTRLHSDVLSFPQMSEQFNQELSLSGKIPSGLFNYVFDFSG
NWKKDASSTKTLAFDGVFISLYTVALEESHMVLCDHVKKAVPSSWEPALLARFMEKFGT
HVIVGVKMGGKDVIYMKQQHASSLEPADVQKKLKEMADKRFLDSKQISQNDTFDITHLR
SADLDTSSSYSYTKNDKEHLLSICRRRGGSDDRNLKHNEWLQTVQSEPDVITMSFVPISLL
LKGVMGSGFLSHAINLYLRYKPPFEELPQFLDFQLPTQWAPVFGLLSRGPQHEQRSVTSLQ
FSFFGTKLYVNTYPVDVGKRPVTGLRLSLNCERNNQLEIHLQHLSAVPKFVQLEDSVTEIL
NFDSHDHKDYEKVQAKNFDHVCTASVESEDEFAIVTGAQLHVGDHGSKKVLFLRLHFSK
LHGCIANRNPEWEVSPVQKLDSSISFMEVVYARQFQVPHAPLHEPKFVGPTETMQKLLKF
VDTTEMKRGPQDSPGYWVVIGARLVVDKGKISLRVKYALPQILIDD

SEQUENCE LISTING

```
<160> NUMBER OF SEQ ID NOS: 12

<210> SEQ ID NO 1
<211> LENGTH: 1758
<212> TYPE: DNA
<213> ORGANISM: Lactuca sativa

<400> SEQUENCE: 1
atggcgctta agcttccagc tgctgaagct gcaaatgttg cgattcagtc aattggatgt      60
ggttatgata tctcgttaga tctgaggctt aattatcgca tgcgtcgtta tcattcagat     120
attggttcta atccatatag aaattgccgt ttgatagaaa ttgaggaaga tgaaggtaga     180
gatattgtgc ttcctggtgg gcttctactt ctcaatgttc ccgaatccat caaatgtcat     240
gaaagcgagc atacacgact tcattctgat gttctttctt ttccgcagat gtcggagcaa     300
ttcaatcagg aattatcatt atccggcaaa attccttcag gcctcttcaa ttatgtgttt     360
gattttctct gaaattggaa gaaagatgca tcaagtacta aaaccctagc tttttgatggt     420 gttttcatct ctttgtacac ggttgcatta gaagaatcac acatggttct ttgtgatcac     480
gtcaagaaag ctgttccatc ttcatgggag cctgctttgt tagcaaggtt tatcgaaaaa     540
tatggcactc atgtaattgt gggtgtaaaa atgggtggaa aagatgtgat atatatgaaa     600
caacagcata catcatccct tgagcctgct gatgtacaga aaaagttaaa ggaaatggca     660
gacaagagat ttttggactc taaacagatt tcacaaaatg acaagtatga catcacacat     720
ctaagatctg cagacttaga cacctctagc tcttattctt acaaggagca tcttttaagc     780
atttgcagaa ggagaggtgg gagtgatgac aggaacctaa aacataacga gtggttacaa     840
accgtacaat cagaaccaga tgtaatcaca atgtcctttg ttccaataag cttgttgcta     900
aagggtgtta tgggaagtgg attcttaagt catgccataa atctttattt acgctataaa     960
cctccatttg aagaccttcc tcagtttctg gacttccagc taccgacaca gtgggcccct    1020
```

-continued

```
gtattcggtt tgttgtctcg tggtccacaa catgagcagc gaagtgtgac atctttacag    1080
ttcagctttt ttgggaccaa gctctacgtg aacacctatc ctgtcgatgt aggtaagagg    1140
cctgtaacag gcctccgact ttccctcaat tgtgaaagaa acaatcagtt agagatccat    1200
ctccagcacc tctccgccgt cccaaaattc gtccaactag aagactccgt aaccgaaatc    1260
ctcaatttcg attcccacga tcataaagac tacgaaaagg tccaagcgaa aaatttcgac    1320
catgtttgca cagccactgt cgagtctgaa gacgaattcg caatcgtaac cggggcccag    1380
ttacatgtcg gggatcacgg gtctaaaaaa gtcctcttcc tacgcctcca cttctcaaaa    1440
ctacatggtt gcatcgcaaa taggaatccg gaatgggaag tgtctccggt tcagaaactg    1500
gattcttcaa tttctttcat ggaggtggtc tacgcacgac aatttcaagt cccgcatgcc    1560
ccacttcacg aaccgaaatt tgtgggcccg acggagacaa tgcagaaact attgaagttt    1620
gtggacacaa cggagatgaa gcggggcccg caagatagcc agggtattg ggttgtcata    1680 ggggctagac ttgttgtgga taagggaaag atttctcttc gagtcaagta cgctttgcct    1740
cagatgttaa cccgatga                                                  1758
```

<210> SEQ ID NO 2
<211> LENGTH: 585
<212> TYPE: PRT
<213> ORGANISM: Lactuca sativa

<400> SEQUENCE: 2

```
Met Ala Leu Lys Leu Pro Ala Ala Glu Ala Ala Asn Val Ala Ile Gln
1               5                   10                  15

Ser Ile Gly Cys Gly Tyr Asp Ile Ser Leu Asp Leu Arg Leu Asn Tyr
            20                  25                  30

Arg Met Arg Arg Tyr His Ser Asp Ile Gly Ser Asn Pro Tyr Arg Asn
        35                  40                  45

Cys Arg Leu Ile Glu Ile Glu Glu Asp Glu Gly Arg Asp Ile Val Leu
    50                  55                  60

Pro Gly Gly Leu Leu Leu Asn Val Pro Glu Ser Ile Lys Cys His
65                  70                  75                  80

Glu Ser Glu His Thr Arg Leu His Ser Asp Val Leu Ser Phe Pro Gln
                85                  90                  95

Met Ser Glu Gln Phe Asn Gln Glu Leu Ser Leu Ser Gly Lys Ile Pro
            100                 105                 110

Ser Gly Leu Phe Asn Tyr Val Phe Asp Phe Ser Gly Asn Trp Lys Lys
        115                 120                 125

Asp Ala Ser Ser Thr Lys Thr Leu Ala Phe Asp Gly Val Phe Ile Ser
    130                 135                 140

Leu Tyr Thr Val Ala Leu Glu Glu Ser His Met Val Leu Cys Asp His
145                 150                 155                 160

Val Lys Lys Ala Val Pro Ser Ser Trp Glu Pro Ala Leu Leu Ala Arg
                165                 170                 175

Phe Ile Glu Lys Tyr Gly Thr His Val Ile Gly Val Lys Met Gly
            180                 185                 190

Gly Lys Asp Val Ile Tyr Met Lys Gln Gln His Thr Ser Ser Leu Glu
        195                 200                 205

Pro Ala Asp Val Gln Lys Lys Leu Lys Glu Met Ala Asp Lys Arg Phe
    210                 215                 220

Leu Asp Ser Lys Gln Ile Ser Gln Asn Asp Lys Tyr Asp Ile Thr His
225                 230                 235                 240
```

Leu Arg Ser Ala Asp Leu Asp Thr Ser Ser Tyr Ser Tyr Lys Glu
            245                 250                 255

His Leu Leu Ser Ile Cys Arg Arg Gly Gly Ser Asp Arg Asn
        260                 265                 270

Leu Lys His Asn Glu Trp Leu Gln Thr Val Gln Ser Glu Pro Asp Val
        275                 280                 285

Ile Thr Met Ser Phe Val Pro Ile Ser Leu Leu Lys Gly Val Met
    290                 295                 300

Gly Ser Gly Phe Leu Ser His Ala Ile Asn Leu Tyr Leu Arg Tyr Lys
305                 310                 315                 320

Pro Pro Phe Glu Asp Leu Pro Gln Phe Leu Asp Phe Gln Leu Pro Thr
                325                 330                 335

Gln Trp Ala Pro Val Phe Gly Leu Leu Ser Arg Gly Pro Gln His Glu
                340                 345                 350

Gln Arg Ser Val Thr Ser Leu Gln Phe Ser Phe Phe Gly Thr Lys Leu
            355                 360                 365

Tyr Val Asn Thr Tyr Pro Val Asp Val Gly Lys Arg Pro Val Thr Gly
        370                 375                 380

Leu Arg Leu Ser Leu Asn Cys Glu Arg Asn Asn Gln Leu Glu Ile His
385                 390                 395                 400

Leu Gln His Leu Ser Ala Val Pro Lys Phe Val Gln Leu Glu Asp Ser
                405                 410                 415

Val Thr Glu Ile Leu Asn Phe Asp Ser His Asp His Lys Asp Tyr Glu
            420                 425                 430

Lys Val Gln Ala Lys Asn Phe Asp His Val Cys Thr Ala Thr Val Glu
        435                 440                 445

Ser Glu Asp Glu Phe Ala Ile Val Thr Gly Ala Gln Leu His Val Gly
    450                 455                 460

Asp His Gly Ser Lys Lys Val Leu Phe Leu Arg Leu His Phe Ser Lys
465                 470                 475                 480

Leu His Gly Cys Ile Ala Asn Arg Asn Pro Glu Trp Glu Val Ser Pro
                485                 490                 495

Val Gln Lys Leu Asp Ser Ser Ile Ser Phe Met Glu Val Val Tyr Ala
            500                 505                 510

Arg Gln Phe Gln Val Pro His Ala Pro Leu His Glu Pro Lys Phe Val
        515                 520                 525

Gly Pro Thr Glu Thr Met Gln Lys Leu Leu Lys Phe Val Asp Thr Thr
    530                 535                 540

Glu Met Lys Arg Gly Pro Gln Asp Ser Pro Gly Tyr Trp Val Val Ile
545                 550                 555                 560

Gly Ala Arg Leu Val Val Asp Lys Gly Lys Ile Ser Leu Arg Val Lys
                565                 570                 575

Tyr Ala Leu Pro Gln Met Leu Thr Arg
            580                 585

<210> SEQ ID NO 3
<211> LENGTH: 1775
<212> TYPE: DNA
<213> ORGANISM: Lactuca serriola

<400> SEQUENCE: 3
atggcgctta agcttccagc tgctgaagct gcaaatgttg cgattcagtc aattggatgt     60
ggttatgata tcgcgttaga tctgaggctt aattatcgca tgcgtcgtta tcattcagat    120

-continued

| | |
|---|---|
| attggttcta atccatatag aaattgccgt tgatagaaa ttgaggaaga tgaaggtaga | 180 |
| gatattgtgc ttcctggtgg gcttctactt ctcaatgttc ccgaatccat caaatgtcat | 240 |
| gaaagcgagt atacacgact tcattctgat gttctttctt ttccgcagat gtcggagcaa | 300 |
| ttcaatcagg aattatcatt atccggcaaa attccttcag gcctcttcaa ttatgtgttt | 360 |
| gattttctg gaaattggaa gaaagatgca tcaagtacta aaaccctagc ttttgatggt | 420 |
| gttttcatct ctttgtacac ggttgcatta aagaatcac acatggttct tgtgatcac | 480 |
| gtcaagaaag ctgttccatc ttcatgggag cctgctttgt tagcaaggtt tatggaaaaa | 540 |
| tttggcactc atgtaattgt gggtgtaaaa atgggtggaa agatgtgat atatatgaaa | 600 |
| caacagcatg catcatccct tgaacctgct gatgtacaga aaagttaaa ggaaatggca | 660 |
| gacaagagat ttttggactc taaacagatt tcacaaaatg acacgtttga catcacacat | 720 |
| ctaagatctg cagacttaga cacctctagc tcttattctt acacaaaaaa tgacaaggag | 780 |
| catcttttaa gcatttgcag aaggagaggt gggagtgatg acaggaacct aaaacataac | 840 |
| gagtggttac aaaccgtaca atcagaacca gatgtaatca caatgtcctt tgttccaata | 900 |
| agcttgttgc taaagggtgt tatgggaagt ggattcttaa gtcatgccat aaatctttat | 960 |
| ttacgctata aacctccatt tgaagagctt cctcagtttc tggacttcca gctaccgaca | 1020 |
| cagtgggccc ctgtattcgg tttgttgtct cgtggtccac aacatgagca gcgaagtgtg | 1080 |
| acatctttac agttcagctt ttttgggacc aagctctacg tgaacaccta tcctgtcgat | 1140 |
| gtaggtaaga ggcctgtaac aggcctccga ctttccctca attgtgaaag aaacaatcag | 1200 |
| ttagagatcc atctccagca cctctccgcc gtcccaaaat tcgtccaact agaagactcc | 1260 |
| gtaaccgaaa tcctcaattt cgattcccac gatcataaag actacgaaaa ggtccaagcg | 1320 |
| aaaaatttcg accatgtttg cacagcctct gtcgagtctg aagacgaatt cgcaatcgta | 1380 |
| accggggccc agttacatgt cggggatcac gggtctaaaa aagtcctctt cctacgcctc | 1440 |
| cacttctcaa aactacatgg ttgcatcgca aataggaatc cggaatggga agtgtctccg | 1500 |
| gttcagaaac tggattcttc aatttctttc atggaggtgg tctacgcacg acaatttcaa | 1560 |
| gtcccgcatg ccccacttca cgaaccgaaa tttgtgggcc cgacggagac gatgcagaag | 1620 |
| ctattgaagt ttgtggacac aacggagatg aagcggggcc cgcaagatag cccagggtat | 1680 |
| tgggttgtaa taggggctag acttgttgtg gataagggaa agatttctct tcgagtcaag | 1740 |
| tacgctttgc ctcagatatt aatcgatgat tagaa | 1775 |

<210> SEQ ID NO 4
<211> LENGTH: 590
<212> TYPE: PRT
<213> ORGANISM: Lactuca serriola

<400> SEQUENCE: 4

```
Met Ala Leu Lys Leu Pro Ala Glu Ala Ala Asn Val Ala Ile Gln
1               5                   10                  15

Ser Ile Gly Cys Gly Tyr Asp Ile Ala Leu Asp Leu Arg Leu Asn Tyr
                20                  25                  30

Arg Met Arg Arg Tyr His Ser Asp Ile Gly Ser Asn Pro Tyr Arg Asn
            35                  40                  45

Cys Arg Leu Ile Glu Ile Glu Glu Asp Glu Gly Arg Asp Ile Val Leu
        50                  55                  60

Pro Gly Gly Leu Leu Leu Leu Asn Val Pro Glu Ser Ile Lys Cys His
65                  70                  75                  80
```

```
Glu Ser Glu Tyr Thr Arg Leu His Ser Asp Val Leu Ser Phe Pro Gln
             85                  90                  95

Met Ser Glu Gln Phe Asn Gln Glu Leu Ser Leu Ser Gly Lys Ile Pro
            100                 105                 110

Ser Gly Leu Phe Asn Tyr Val Phe Asp Phe Ser Gly Asn Trp Lys Lys
            115                 120                 125

Asp Ala Ser Ser Thr Lys Thr Leu Ala Phe Asp Gly Val Phe Ile Ser
130             135                 140

Leu Tyr Thr Val Ala Leu Glu Glu Ser His Met Val Leu Cys Asp His
145                 150                 155                 160

Val Lys Lys Ala Val Pro Ser Ser Trp Glu Pro Ala Leu Leu Ala Arg
                165                 170                 175

Phe Met Glu Lys Phe Gly Thr His Val Ile Val Gly Val Lys Met Gly
                180                 185                 190

Gly Lys Asp Val Ile Tyr Met Lys Gln Gln His Ala Ser Ser Leu Glu
            195                 200                 205

Pro Ala Asp Val Gln Lys Lys Leu Lys Glu Met Ala Asp Lys Arg Phe
210             215                 220

Leu Asp Ser Lys Gln Ile Ser Gln Asn Asp Thr Phe Asp Ile Thr His
225                 230                 235                 240

Leu Arg Ser Ala Asp Leu Asp Thr Ser Ser Ser Tyr Ser Tyr Thr Lys
                245                 250                 255

Asn Asp Lys Glu His Leu Leu Ser Ile Cys Arg Arg Gly Gly Ser
            260                 265                 270

Asp Asp Arg Asn Leu Lys His Asn Glu Trp Leu Gln Thr Val Gln Ser
            275                 280                 285

Glu Pro Asp Val Ile Thr Met Ser Phe Val Pro Ile Ser Leu Leu Leu
290                 295                 300

Lys Gly Val Met Gly Ser Gly Phe Leu Ser His Ala Ile Asn Leu Tyr
305                 310                 315                 320

Leu Arg Tyr Lys Pro Pro Phe Glu Glu Leu Pro Gln Phe Leu Asp Phe
                325                 330                 335

Gln Leu Pro Thr Gln Trp Ala Pro Val Phe Gly Leu Leu Ser Arg Gly
                340                 345                 350

Pro Gln His Glu Gln Arg Ser Val Thr Ser Leu Gln Phe Ser Phe Phe
            355                 360                 365

Gly Thr Lys Leu Tyr Val Asn Thr Tyr Pro Val Asp Val Gly Lys Arg
            370                 375                 380

Pro Val Thr Gly Leu Arg Leu Ser Leu Asn Cys Glu Arg Asn Asn Gln
385                 390                 395                 400

Leu Glu Ile His Leu Gln His Leu Ser Ala Val Pro Lys Phe Val Gln
                405                 410                 415

Leu Glu Asp Ser Val Thr Glu Ile Leu Asn Phe Asp Ser His Asp His
                420                 425                 430

Lys Asp Tyr Glu Lys Val Gln Ala Lys Asn Phe Asp His Val Cys Thr
            435                 440                 445

Ala Ser Val Glu Ser Glu Asp Glu Phe Ala Ile Val Thr Gly Ala Gln
450                 455                 460

Leu His Val Gly Asp His Gly Ser Lys Lys Val Leu Phe Leu Arg Leu
465                 470                 475                 480

His Phe Ser Lys Leu His Gly Cys Ile Ala Asn Arg Asn Pro Glu Trp
                485                 490                 495

Glu Val Ser Pro Val Gln Lys Leu Asp Ser Ser Ile Ser Phe Met Glu
```

```
            500                 505                 510
Val Val Tyr Ala Arg Gln Phe Gln Val Pro His Ala Pro Leu His Glu
        515                 520                 525

Pro Lys Phe Val Gly Pro Thr Glu Thr Met Gln Lys Leu Leu Lys Phe
        530                 535                 540

Val Asp Thr Thr Glu Met Lys Arg Gly Pro Gln Asp Ser Pro Gly Tyr
545                 550                 555                 560

Trp Val Val Ile Gly Ala Arg Leu Val Val Asp Lys Gly Lys Ile Ser
                565                 570                 575

Leu Arg Val Lys Tyr Ala Leu Pro Gln Ile Leu Ile Asp Asp
            580                 585                 590

<210> SEQ ID NO 5
<211> LENGTH: 23
<212> TYPE: DNA
<213> ORGANISM: Artificial Sequence
<220> FEATURE:
<223> OTHER INFORMATION: MACPF1R_F primer

<400> SEQUENCE: 5
tttcacaaaa tgacacgttt gac                                            23

<210> SEQ ID NO 6
<211> LENGTH: 22
<212> TYPE: DNA
<213> ORGANISM: Artificial Sequence
<220> FEATURE:
<223> OTHER INFORMATION: MACPF1R_R primer

<400> SEQUENCE: 6
tgcttaaaag atgctccttg tc                                             22

<210> SEQ ID NO 7
<211> LENGTH: 22
<212> TYPE: DNA
<213> ORGANISM: Artificial Sequence
<220> FEATURE:
<223> OTHER INFORMATION: MACPF 1 forward primer

<400> SEQUENCE: 7
acatcacaca tctaagatct gc                                             22

<210> SEQ ID NO 8
<211> LENGTH: 22
<212> TYPE: DNA
<213> ORGANISM: Artificial Sequence
<220> FEATURE:
<223> OTHER INFORMATION: MACPF 1 Reverse primer

<400> SEQUENCE: 8
atggaggttt atagcgtaaa ta                                             22

<210> SEQ ID NO 9
<211> LENGTH: 20
<212> TYPE: DNA
<213> ORGANISM: Artificial Sequence
<220> FEATURE:
<223> OTHER INFORMATION: B. lactucae actin Forward primer

<400> SEQUENCE: 9
gcgagaaatt gtgcgtgata                                                20

<210> SEQ ID NO 10
```

```
<211> LENGTH: 20
<212> TYPE: DNA
<213> ORGANISM: Artificial Sequence
<220> FEATURE:
<223> OTHER INFORMATION: B. lactucae actin Reverse primer

<400> SEQUENCE: 10
actcggctgc agtcttcatt                                               20

<210> SEQ ID NO 11
<211> LENGTH: 24
<212> TYPE: DNA
<213> ORGANISM: Artificial Sequence
<220> FEATURE:
<223> OTHER INFORMATION: LsTUA-3F primer

<400> SEQUENCE: 11
cttcttagtg ttcaatgctg ttgg                                          24

<210> SEQ ID NO 12
<211> LENGTH: 24
<212> TYPE: DNA
<213> ORGANISM: Artificial Sequence
<220> FEATURE:
<223> OTHER INFORMATION: LsTUA-3R primer

<400> SEQUENCE: 12
gaagggtaga tagtgaaacc gagc                                          24
```

US 11,920,144 B2

RESISTANCE GENE AND LETTUCE PLANT RESISTANT TO DOWNY MILDEW

CROSS-REFERENCE TO RELATED APPLICATIONS

This application is the United States national phase of International Application No. PCT/EP2018/072249 filed Aug. 16, 2018, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2100639_ST25.txt. The size of the text file is 16,774 bytes, and the text file was created on Feb. 2, 2021.

DESCRIPTION

The present invention relates to a lettuce plant that is resistant to downy mildew, more specifically to a lettuce plant that comprises a mutated gene that confers broad spectrum resistance to oomycetes in lettuce. Furthermore the present invention relates a resistance gene and a method for obtaining a lettuce plant that is resistant to downy mildew, wherein the method comprises the step of mutating a gene.

Downy mildew refers to several types of oomycete microbes that are parasites of plants. Downy mildew can originate from various species, but mainly of *Peronospora, Plasmopara* and *Bremia*. Downy mildew is a problem in many food crops, in for example in lettuce caused by *Bremia lactucae*, affecting the production of this crop worldwide. Plants that are being affected include food crops such as brassicas (e.g. cabbage), potatoes, grape, spinach, lettuce, onion, tomato, cucumber plants. Downy mildew infection show symptoms of discoloured areas on upper leaf surfaces in combination with white, grey or purple mould located on the other side of the leaf surface below. Disease is spread from plant to plant by airborne spores.

Lettuce, mostly known as *Lactuca sativa*, but also including *Lactuca* species such as *L. serriola, L. saligna* or *L. virosa*, is a very important crop worldwide. Some of the most popular varieties available are Iceberg, Romaine, Butterhead, Batavia and Oakleaf. There are many plant pathogens that affect *L. sativa*, and some of the diseases caused by these pathogens are downy mildew, sclerotinia rot, powdery mildew, fusarium wilt of which the most important disease is lettuce downy mildew, which is caused by the *B. lactucae*, an oomycete pathogen that belong to Peronosporaceae.

For some vegetable crops, such as lettuce, cultivars with resistance to downy mildew are available. However, the pathogen under pressure will mutate to break down the disease resistance and new disease resistance in crops is needed to control infection. Especially in lettuce the occurrence of resistant downy mildew is particularly complex as there are many different races, and new resistant downy mildew species emerging all the time.

In lettuce, infection of *B. lactucae* result in yellow to pale green lesions that eventually become necrotic due to secondary pathogens leading to major crop losses. Fungicides can be used to control *B. lactucae*, but eventually *B. lactucae* becomes immune to these chemicals, because over time the pathogen also acquires resistance to fungicides. Furthermore, there are multiple lettuce varieties available that are resistant to *B. lactucae* but resistance is quickly overcome because new *Bremia* races develop rapidly. Therefore, it is of the utmost importance to find other methods to control *B. lactucae* infection. Most preferably is to identify a resistance gene that gives broad resistance against *B. lactucae* and to provide for lettuce plants that are resistant to downy mildew. Therefore, identification of resistance genes is a promising alternative.

SUMMARY

Considering the above, there is a need in the art for to provide plants that are resistant to downy mildew and wherein plants have a broad spectrum resistance against this pathogen. Furthermore, it is an object of present invention to provide a method to obtain such downy mildew resistant plants.

It is an object of the present invention, amongst other objects, to address the above need in the art. The object of present invention, amongst other objects, is met by the present invention as outlined in the appended claims.

BRIEF DESCRIPTION OF THE DRAWINGS

The present invention will be further detailed in the following examples and figures wherein:

FIG. 3: shows an overview of the disease test performed with the most recent isolates of *Bremia* Bl16 to 33 on *L. sativa* lines Cobham Green, Green Towers, Vanity and SE01. SE01 is a lettuce plant (*L. sativa*) of present invention comprising the MACPF1R resistance gene. The plant of present invention shows to be fully resistant to all downy mildew isolates, whereas the other lines show to be susceptible to the downy mildew isolates.

FIG. 4: shows a table of the mutations of present invention and their positions in the MACPF1R protein (SEQ ID NO: 4).

FIG. 5: shows the alignment of the amino acid sequence of MACPF1 (SEQ ID NO: 2) and the MACPF1R (SEQ ID NO:SEQ ID NO: 4) protein. Differences between the two protein sequences have been indicated in grey and correspond with the information as presented in FIG. 4.

FIG. 6: shows the cDNA sequence (SEQ ID NO: 1) encoded by the MACPF1 gene of *Lactuca sativa*.

FIG. 7: shows the protein sequence (SEQ ID NO: 2) encoded by the MACPF1 gene of *Lactuca sativa*.

FIG. 8: shows the cDNA sequence (SEQ ID NO: 3) encoded by the MACPF1R gene of *Lactuca serriola*.

FIG. 9: shows the protein sequence (SEQ ID NO: 4) encoded by the MACPF1R gene of *Lactuca serriola*.

DETAILED DESCRIPTION

Figure 1:
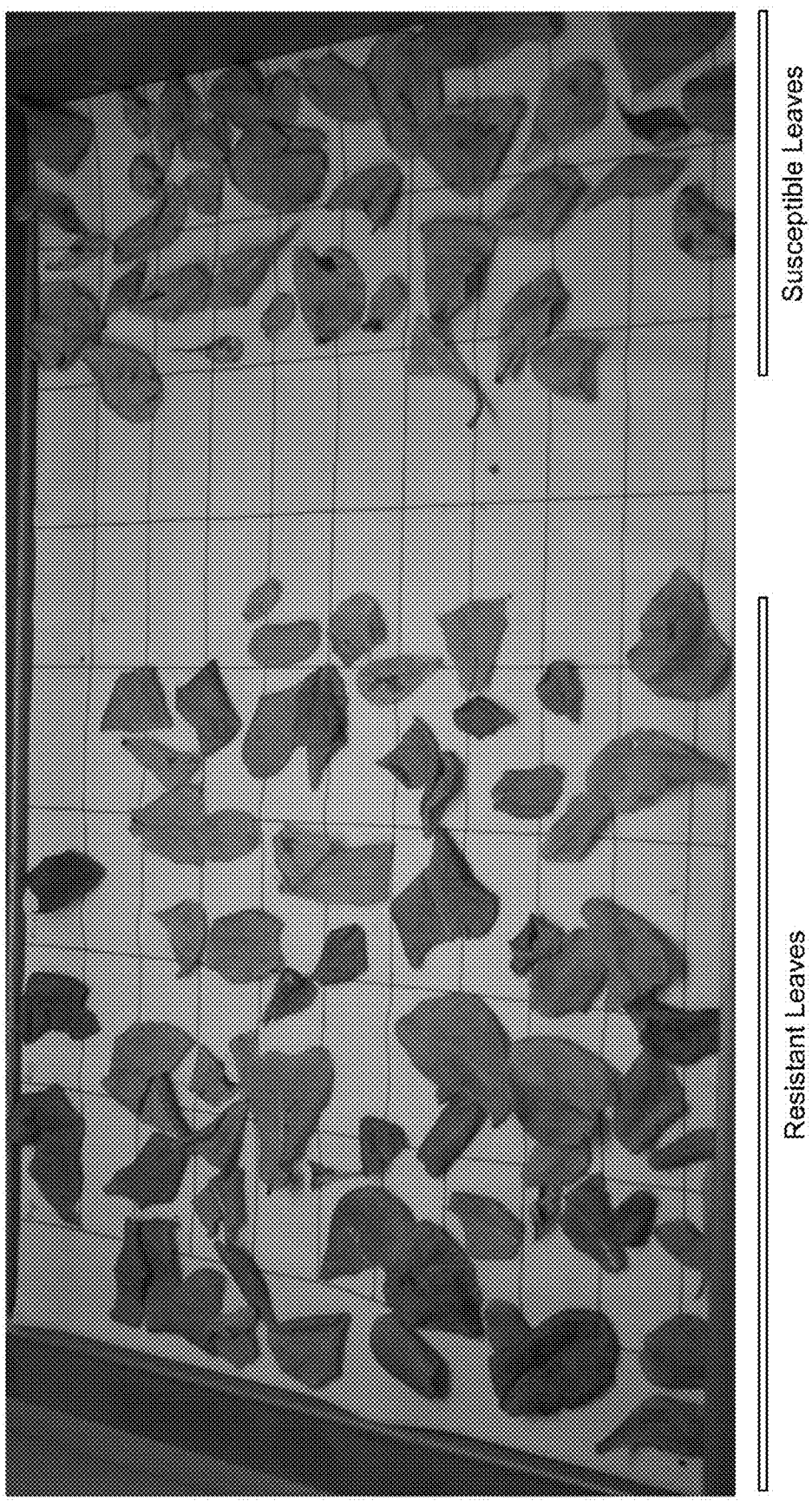
FIG. 1: shows leaves of *L. sativa* plants that are resistant (left) or susceptible (right) to *Bremia lactucae*. All lettuce plants comprised the MACPFR1 resistance gene. Subsequently this MACPF1R gene has been silenced in these plants using VIGS gene silencing and infected with *Bremia lactucae*. As expected with transient gene silencing, VIGS gene silencing does not result in fully 100% silencing of the MACPF1R gene in all plants. The leaves on the right originate from plants, wherein the resistance gene has been silenced by VIGS silencing, therefore the MACPF1R gene expression was reduced. The leaves on the left originate from plants wherein VIGS silencing was less successful in reducing the MACPF1R gene expression, therefore there is still a significant amount of MACPF1R gene expression in these plants. Leaves of the plants (right) wherein the resistance gene was silenced showed to be susceptible to downy mildew. The MACPF1R expression levels in the leaves of both groups (plants that showed to be resistant or susceptible to downy mildew) were collected and RNA was isolated to determine the expression levels of the resistance gene by qPCR (see FIG. 2).

Specifically, the above object, amongst other objects, is met, according to a first aspect, by the present invention by a lettuce plant that is resistant to downy mildew, wherein said plant comprises one or more mutations in a MACPF1 gene, wherein said MACPF1 gene encodes for a protein sequence having at least 90% sequence identity with SEQ ID NO: 2, preferably at least 95%, more preferably at least 98%, most preferably at least 99%.

Research on the MACPF (Membrane Attack Complex/Perforin) superfamily is mainly focused on its function in humans where it plays a role in the immune system in defeating virus and bacteria related diseases. The MACPF superfamily is named after a domain that is common to the membrane attack complex (MAC) proteins of complement and Perforin. Many members are important pore forming toxins in eukaryotes. The archetypal members of the family are complement C9 and Perforin, both of which function in human immunity. C9 functions by punching holes in the membranes of Gram-negative bacteria. Perforin is released by cytotoxic T cells and lyses virally infected and transformed cells. In addition Perforin permits delivery of cytotoxic proteases called granzymes that cause cell death.

The majority of disease resistance genes in plants encode nucleotide-binding site leucine-rich repeat proteins, also known as NBS-LRR proteins (encoded by R genes). These proteins are characterized by nucleotide-binding site (NBS) and leucine-rich repeat (LRR) domains as well as variable amino- and carboxy-terminal domains and are involved in the detection of diverse pathogens, including bacteria, viruses, fungi, nematodes, insects and oomycetes. There are two major subfamilies of plant NBS-LRR proteins defined by the Toll/interleukin-1 receptor (TIR) or the coiled-coil (CC) motifs in the amino-terminal domain and are both involved in pathogen recognition. The MACPF1R gene is involved in a completely different mechanism than the known NBS-LRR mechanism (R genes) in the plant. Therefore, the presence of the MACPF1R resistance gene will decrease the chances of the pathogen overcoming the resistance, as often seen with the R genes. Even so, combined with R genes, disease resistance (e.g. against downy mildew) may even be further improved.

The identification of a novel candidate dominant resistance gene, indicated here as the MACPF1R gene is obtained by gene mapping of multiple independent downy mildew resistance genes in Lettuce. For the first time a MACPF gene has been found in plants that can be linked to plant disease resistance. Using gene mapping methods a gene region was disclosed in lettuce which hosts a number of novel annotated genes that are associated with pathogen resistance, called the membrane attack complex and Perforin (MACPF) gene. In lettuce there are five MACPF homologs present in the lettuce genome, 4 are clustered on chromosome 9 and one is present on chromosome 7. Only one of them is involved with this *Bremia* resistance phenotype, MACPF1R. This MACPF1R gene of present invention gives resistance to all *Bremia* races Bl 1 to 33, preferably Bl 1 to 35, more preferably a broad spectrum *Bremia lactucae* resistance.

To demonstrate that the MACPF1 gene family is related to *Bremia* resistance, the putative resistance genes (MACPF1R) have been silenced by tobacco rattle virus (TRV)-based virus-induced gene silencing (VIGS) to induce susceptibility to *B. lactucae* infection in resistant *L. serriola* lettuce lines containing the MACPFR1 resistance gene. With VIGS it was demonstrated that the MACPF1R gene was associated with downy mildew resistance, VIGS gene silencing was used to create *Bremia*-susceptibility in resistant *Lactuca* species. Resistant lettuce plants were transient transformed with a MACPF1R silencing construct. With VIGS, resistant lettuce lines (*L. serriola*) were made susceptible by removing the MACPF1R gene via virus induced gene silencing, thereby silencing the MACPF1R gene.

Furthermore it was shown by stable transformation of MACPF1R gene in the susceptible parent (*L. sativa*) that when MACPF1R was segregating in the next generation it resulted in resistant plants when MACPF1R was present.

According to another preferred embodiment, the present invention relates to the Lettuce plant, wherein the mutations in the MACPF1 gene result in amino acid changes comprised of amino acid substitutions on the amino acid positions 25, 84, 178, 181, 204, 235, 236, 329, 450, 586, 588, and 589 in the MACPF1 protein represented by SEQ ID NO:2.

According to yet another preferred embodiment, the present invention relates to the Lettuce plant, wherein the mutations in the MACPF1 gene result in amino acid changes further comprised of an addition on amino acid position 590 in the MACPF protein represented by SEQ ID NO:2.

According to yet another preferred embodiment, the present invention relates to the Lettuce plant, wherein the mutations in the MACPF1 gene result in amino acid changes are further comprised of an insertion of four amino acids on the positions 255 to 258 in the MACPF1 protein represented by SEQ ID NO:2.

According to another preferred embodiment, the present invention relates to the Lettuce plant, wherein the MACPF1 gene that comprises one or more mutations encodes for the protein sequence represented by SEQ ID NO: 4. Sequencing experiments showed that the protein encoded by the MACPF1R gene from the resistant plant compared with the protein encoded by the MACPF gene of a plant that is susceptible differs in 12 amino acid substitutions, one amino acid addition and an insertion of 4 amino acids; the gene (MACPF1R) that encodes for the protein that comprises all the above mutations is represented by SEQ ID NO: 3. The mutated protein is represented by SEQ ID NO: 4.

According to yet another preferred embodiment, the present invention relates to the lettuce plant, wherein the plant is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa.*

According to a preferred embodiment, the present invention relates to the lettuce plant, wherein the mutations in the MACPF1 gene are obtained by gene editing techniques, preferably by mutagenesis and/or CRISPR/Cas.

According to another preferred embodiment, the present invention relates to the Lettuce plant, wherein the downy mildew is caused by an oomycete, more preferably *Bremia lactucae*.

According to another preferred embodiment, the present invention relates to the lettuce plant, wherein the lettuce plant is resistant to downy mildew caused by one or more of *Bremia lactucae* selected from the group of race Bl1 to Bl33. The resistant lettuce plant of present invention is resistance to all *Bremia* races Bl1 to Bl33, preferably Bl1 to Bl35, more preferably broad spectrum *Bremia lactucae* resistant.

According to yet another preferred embodiment, the present invention relates to the lettuce plant, wherein the resistance gene MACPF1R is obtainable from deposit number NCIMB 42435.

The present invention, according to a second aspect, relates to seed produced by the lettuce plant of present invention.

The present invention, according to a third aspect, relates to a resistance gene MACPF1R that confers broad spectrum resistance to oomycetes in lettuce plants, wherein the gene comprises a coding sequence that has at least 90% sequence identity with SEQ ID NO:3, preferably at least 95%, more preferably at least 98%, most preferably at least 99%, most preferably 100%. SEQ ID NO:3 represents the coding nucleotide sequence of MACPF1R resistance gene of *Lactuca serriola* and encodes for the MACPF1R protein sequence represented by SEQ ID NO:4. SEQ ID NO:4 represents the MACPF1R protein sequence of *Lactuca serriola* and lettuce plants that express this protein show complete resistance to downy mildew.

According to a preferred embodiment, the present invention relates to resistance gene MACPF1R, wherein the gene encodes for a MACPF1R protein that has at least 85% sequence identity with SEQ ID NO: 4, preferably at least 90%, more preferably at least 95%, most preferably at least 98%, most preferably 100%.

According to another preferred embodiment, the present invention relates to the resistance gene MACPF1R, wherein broad spectrum resistance to oomycetes in lettuce comprises resistance to *Bremia lactucae* of race Bl1 to Bl33.

According to yet another preferred embodiment, the present invention relates to the resistance gene MACPF1R, wherein the plant is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa*.

The present invention, according to a further aspect, relates to a seed produced by a lettuce plant of present invention.

The present invention, according to a further aspect, relates to a method for obtaining a lettuce plant that is resistant to downy mildew, wherein the method comprises the steps of,
a) crossing a lettuce plant comprised of the resistance gene MACPF1R of present invention with a lettuce plant that is not resistant to oomycetes,
b) optionally, selfing the plant obtained in step a) for at least one time,
c) selecting the plants that are resistant to downy mildew.
In the method of present invention the lettuce plant is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa*.

The present invention, according to a further aspect, relates to a method for obtaining a lettuce plant that is resistant to downy mildew, wherein the method comprises the step of providing one or more mutations in a MACPF1 gene of a lettuce plant, resulting in a MACPF1R resistance gene of present invention. The MACPF1 gene comprises a coding sequence that has at least 90% sequence identity with SEQ ID NO: 1, preferably at least 95%, more preferably at least 98%, most preferably at least 99%, most preferably 100%. SEQ ID NO:1 represents the coding nucleotide sequence of the MACPF1 gene of *Lactuca sativa*. This sequence is the wild type sequence and does not contain the mutations as compared to the resistance (MACPF1R) gene of present invention.

According to another preferred embodiment, the present invention relates to the method, wherein the mutations in the MACPF1 gene result in amino acid changes comprised of amino acid substitutions on the amino acid positions 25, 84, 178, 181, 204, 235, 236, 329, 450, 586, 588, and 589 in the MACPF1 protein represented by SEQ ID NO:2. SEQ ID NO:2 represents the MACPF1 protein sequence of *Lactuca sativa*. This protein sequence does not comprise the mutations as compared to the MACPF1R protein of present invention. Therefore, *L. sativa* that express the protein of SEQ ID NO:2 is susceptible to downy Mildew. SEQ ID NO:2 represent the wild type protein sequence as found in lettuce (*Lactuca sativa*) that does not contain the mutations that result into the MACPF1R protein (SEQ ID NO: 4). Preferably the amino acid substitutions are S→A, H→Y, I→M, Y→F, T→A, K→T, Y→F, D→E, T→S, M→I, T→I, R→D, respectively on the amino acid position 25, 84, 178, 181, 204, 235, 236, 329, 450, 586, 588, and 589 in the MACPF1 protein. Table 8 shows an overview of the mutations in the MACPF1 protein in their respective positions. The mutated MACPF1 protein (MACPF1R) is represented by SEQ ID NO:4.

According to yet another preferred embodiment, the present invention relates to the method, wherein the mutations in the MACPF1 gene result in amino acid changes further comprised of an addition, preferably of Aspartic Acid (D), on amino acid position 590 in the MACPF1 protein represented by SEQ ID NO:2.

According to a preferred embodiment, the present invention relates to the method, wherein the mutations in the MACPF1 gene result in amino acid changes further comprised of an insertion of four amino acids on the positions 255 to 258 in the MACPF1 protein represented by SEQ ID NO:2. The insertion of four amino acids is preferably TKND.

According to a preferred embodiment, the present invention relates to the method, wherein the mutations in the MACPF1 gene results in a protein represented by SEQ ID NO: 4.

According to another preferred embodiment, the present invention relates to the method, wherein the lettuce plant is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa*.

A lettuce plant comprised of the insertion of 4 amino acids in combination with an addition, in combination with the amino acid substitutions gives a high downy mildew resistance phenotype. A plant having this resistant phenotype can be obtained via use of gene editing and/or mutation techniques, such as EMS mutagenesis or CRISPR/Cas in concert with cloning techniques on the MACPF1 gene to generate disease resistant crops.

According to yet another preferred embodiment, the present invention relates to the method, wherein the mutations in the MACPF1 gene are obtained by gene editing techniques, preferably by mutagenesis and/or CRISPR/Cas. Alternatively, a MACPF1R gene can be brought into the plant by means of transgenic techniques or by introgression.

According to another preferred embodiment, the present invention relates to the method, wherein the mutations in the MACPF1 gene are non-natural mutations. Mutations induced by gene editing techniques such as mutagenesis, CRISPR/Cas, transgenic techniques, or others can be regarded as non-natural mutations.

The present invention, according to a further aspect, relates to the use of a plasmid for introducing a resistance gene into the genome of a plant or plant cell, wherein the plasmid comprises the resistance gene MACPF1R of present invention. The resistance gene of present invention may be transferred (e.g. by transformation or transfection) into plants, such as lettuce plants, using a plasmid that comprises the MACPF1R resistance gene of present invention wherein the gene comprises a coding sequence that has at least 90% sequence identity with SEQ ID NO: 3. The resistance gene MACPF1R encodes for a MACPF1R protein that has at least 85% sequence identity with SEQ ID NO: 4. The Resistance gene MACPF1R, after being transferred into the plant would provide broad spectrum resistance to oomycetes, i.e. resistance to *Bremia lactucae* of race Bl1 to Bl33.

EXAMPLES

Synthesis of Construct MACPF1R.

In order to study the function of the MACPF1R gene and more specifically if the amino acid substitutions, additions and/or the amino acid insertion are causing the resistance, the MACPF1R construct has been developed. To study if the insertion or the amino acid substitution+addition is effecting resistance, three constructs were made: one with the resistance gene of present invention, one construct with the insertion and no substitutions or additions called LsMACPF1Ins and one construct with the substitution+addition and not the insertion called LsMACPF1Sub. Synthetically constructs with gateway sites were made by Gen9. These fragments were cloned into the vector pK7WG2,0 and transformed to A.tum GV2260. Finally those constructs were stably transformed into *L. sativa* cultivars Cobham Green and Wendel. The differences between the MACPF1 and MACPF1R protein are 12 amino acid substitutions, an amino acid addition and an insertion of 4 amino acids, see FIG. 4 and FIG. 5 for the specific mutations in the protein and their positions.

Transformation into Lettuce to Study MACPF1R Function

The multiple constructs of above of the MACPF1 gene were transformed into lettuce (*L. sativa*) using co-cultivation with agrobacterium. The following construct were used:
1) The MACPF1R gene, called "LsMACPF1R" (=MACPF1 gene wherein insertion, addition and substitutions are present),
2) The MACPF1R gene without the insertion, called "LsMACPF1Sub",
3) The MACPF1R gene without substitutions and addition, called "LsMACPF1Ins".

Furthermore, it was shown by stable transformation of MACPF1R gene in the susceptible parent (*L. sativa*) that when MACPF1R was segregating in the next generation it resulted in resistant plants when the MACPF1R resistance gene was present. This was followed by primers specific for the MACPF1R gene. Sequences are present in table 1. Plants were selected based on the primers below in table 1 (SEQ ID NO: 5 and SEQ ID NO: 6, respectively).

TABLE 1

| Primer name | Sequence |
|---|---|
| MACPF1R_F | 5'- TTTCACAAAATGACACGTTTGAC -3' (SEQ ID NO: 5) |
| MACPF1R_R | 5'- TGCTTAAAAGATGCTCCTTGTC -3' (SEQ ID NO: 6) |

MACPF1R Silencing Experiment Using Virus Induced Gene Silencing (VIGS)

Tobacco rattle virus (TRV)-derived VIGS vectors have been abundantly described to study gene function in *Arabidopsis thaliana, Nicotiana benthamiana, Lycopersicon esculentum* and other plants (see for example Huang C, Qian Y, Li Z, Zhou X.: Virus-induced gene silencing and its application in plant functional genomics. Sci China Life Sci. 2012; 55(2):99-108). Briefly, lines containing MACPF1R were silenced for MACPF1 by VIGS. Independent of MACPF1R silencing the PDS gene is silenced as well that serves as positive control to indicate if VIGS is working. PDS is involved in carotenoid biosynthesis and is the first step in lycopene biosynthesis. This step is catalyzed by phytoene desaturase (PDS). When silencing of the PDS gene is achieved, this results in bleached leaves. Silencing of MACPF1R did not result in a visual phenotype. Therefore, all plants that were MACPF1-VIGS inoculated were harvested and put in a tray and sprayed with *Bremia* Bl30. This resulted in susceptible leaves while non-silenced MACPF1 plants stayed resistant.

Resistance Test/Biotest for Downy Mildew in Lettuce

The MACPF1 constructs (LsMACPF1R, -Ins and -Sub) were introduced in lettuce lines using co-cultivation with agrobacterium to get stable transformants. Introducing of the MACPF1R consensus sequence stable transformed in *Bremia* susceptible lettuce lines (Cobham Green and Wendel) result in *Bremia* resistant lines in T0, T1 and T2 generation. Outcome of the results are lettuce T1 plants containing the different constructs which are tested for resistance to the oomycete *Bremia*.

For LsMACPF1Ins, 47 independent lines in the Cobham Green background and 9 independent lines in the Wendel background were made. In the case of LsMACPF1Sub 57 independent lines in Cobham Green background and 8 independent lines in the Wendel background were made. The seeds of those independent lines were tested in a *Bremia* seedling test in which 50 seeds per transformant were inoculated with *Bremia*. The results are that all plants (Wendel and Cobham Green) were susceptible for *Bremia* (Bl24 *Bremia* tested in Wendel, Bl24 and BL32 *Bremia* tested in Cobham Green).

The above experiments indicate that both substitutions, addition and the insertion in the MACPF1 gene/protein are necessary to provide the full resistant phenotype to *Bremia*. If we isolate only the insertion or only the substitution+addition from the resistant source, the *Bremia* resistance is lost. Therefore the substitutions, addition and insertion are needed to be present in the MACPF1 protein to make an active MACPF1R protein to form pores which could give resistance to *Bremia* in lettuce.

Leaves of resistant plants stably transformed with or without VIGS MACPF1, were put in trays with moistened paperboard. The infected seedlings are suspended in 20 mL water, filtered by cheesecloth and the flow-through is collected in a spray flask. One tray is spray-inoculated with this B. lactucae suspension. The trays are covered with a glass plate and stored in a climate chamber at 15° C. (12 hours of light). A black, opaque foil is placed over the trays for one day to improve growth of B. lactucae. After one day, the foil is removed. Eight to ten days after infection leaves are phenotypically scored by eye on the presence of Bremia and qPCR was performed to determine MACPF1R expression.

Expression of MACPF1R Genes in Lettuce

A number of gene expression experiments were conducted in lettuce tissues obtained form the VIGS experiment as outlined above, to determine MACPF1R expression. The response of lettuce leaf discs to Bremia lactucae infection was examined and gene expression studies were used to assess VIGS analysis.

To create more insight in the response of lettuce to infection with Bremia (Bremia lactucae), leaves of resistant and susceptible plants were harvested. cDNA was synthesized from RNA that had been isolated from infected leaf discs. The expression of MACPF1 was assessed in lettuce by conducting qPCR. Expression of Bremia lactucae actin and expression of MACPF1 were analyzed by qPCR using the primers as set out in Table 2 (SEQ ID NO: 6, SEQ ID NO: 7, SEQ ID NO: 8, SEQ ID NO: 9, SEQ ID NO: 10, SEQ ID NO: 11, and SEQ ID NO: 12, respectively). This experiment was performed independent in duplo.

TABLE 2

| Primer name | Sequence |
| --- | --- |
| MACPF 1 Fwd | 5'-ACATCACACATCTAAGATCTGC-3' (SEQ ID NO: 7) |
| MACPF 1 Rv | 5'-ATGGAGGTTTATAGCGTAAATA-3' (SEQ ID NO: 8) |
| B. lactucae Actin Fwd | 5'-GCGAGAAATTGTGCGTGATA-3' (SEQ ID NO: 9) |
| B. lactucae Actin Rv | 5'-ACTCGGCTGCAGTCTTCATT-3' (SEQ ID NO: 10) |
| LsTUA-3F | 5'-CTTCTTAGTGTTCAATGCTGTTGG-3' (SEQ ID NO: 11) |
| LsTUA-3R | 5'-GAAGGGTAGATAGTGAAACCGAGC-3' (SEQ ID NO: 12) |

Figure 2:
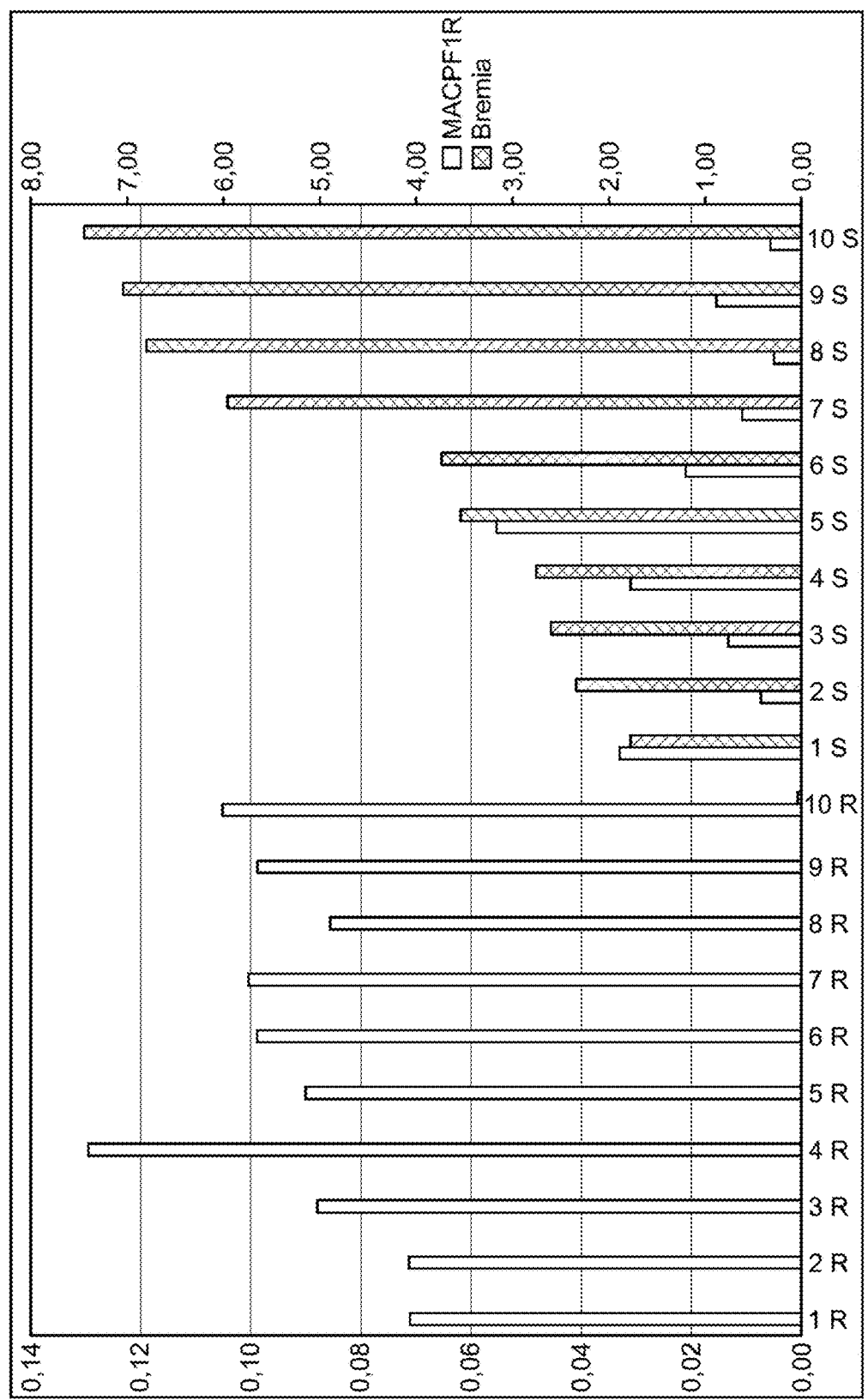
FIG. 2: shows MACPF1R expression levels in MACPF1R VIGS silenced lettuce lines infected with *Bremia* (Bl30). The transcription levels, determined by qPCR, of MACPF1R resistance gene in relation to the transcription levels of a house keeping gene (TUA-3). The transcription levels of *Bremia lactuca* was determined by the transcripts of a *Bremia* house keeping gene (Actin) in relation to the lettuce house keeping gene TUA-3 of *Bremia lactucae* were determined in leave samples of *L. sativa* plants of the experiment of FIG. 1. Leaves of the plants that were resistant to *Bremia lactucae* showed to have a high MACPF1R gene expression and low transcriptional levels of the *Bremia lactucae* house keeping gene. Leaves of the plant that were 3usceptible to *Bremia lactucae*, showed low MACPF1 gene expression and high transcriptional levels of the *Bremia lactucae* house keeping gene, indicating the susceptibility corresponds with low MACPF1R gene expression.

Results (FIG. 2) shows that in leaves of the plants that are resistant to Bremia little to no Bremia was detected and that the level of MACPF1R was very high. The leaves that originate from plants that are susceptible to Bremia, showed the opposite pattern, a high level of Bremia and low levels of MACPF1R expression.

The invention claimed is:

1. A lettuce plant that is resistant to downy mildew, wherein said plant comprises a MACPF1R resistance gene, wherein said MACPF1R resistance gene encodes for the protein sequence of SEQ ID NO: 4, wherein the lettuce plant is not *Lactuca serriola*.

2. The lettuce plant according to claim 1, wherein the lettuce plant is selected from *Lactuca sativa, Lactuca virosa, Lactuca saligna, Lactuca aculeate, Lactuca georgica, Lactuca perennis, Lactuca tatarica*, and *Lactuca viminea*.

3. The lettuce plant according to claim 1, wherein the downy mildew is caused by *Bremia lactucae*.

4. The lettuce plant according to claim 1, wherein the lettuce plant is resistant to downy mildew caused by one or more of *Bremia lactucae* races Bl1 to Bl33.

5. A seed produced by a lettuce plant according to claim 1, wherein said seed comprises a MACPF1R resistance gene, wherein said MACPF1R resistance gene encodes for the protein sequence of SEQ ID NO: 4.

6. A method for obtaining a lettuce plant that is resistant to downy mildew, wherein the method comprises the steps of, a) crossing a lettuce plant comprising a MACPF1R resistance gene—that encodes for the protein sequence of SEQ ID NO: 4 with a lettuce plant that is not resistant to oomycetes, b) optionally, selfing the plant obtained in step a) for at least one time, and c) selecting a plant obtained from step a) or step b) that are resistant to downy mildew.

7. A method for obtaining a lettuce plant that is resistant to downy mildew, wherein the method comprises a step of mutating a MACPF1 gene of a lettuce plant, resulting in a MACPF1R resistance gene that encodes for the protein sequence of SEQ ID NO: 4.

8. The method according to claim 7, wherein the lettuce plant is selected from *Lactuca sativa, Lactuca virosa, Lactuca saligna, Lactuca aculeate, Lactuca georgica, Lactuca perennis, Lactuca tatarica*, and *Lactuca viminea*.

9. The method according to claim 7, wherein the MACPF1R resistance gene is obtained by gene editing techniques.

* * * * *